United States Patent
Shumaker-Parry et al.

(10) Patent No.: US 7,999,025 B2
(45) Date of Patent: Aug. 16, 2011

(54) ASYMMETRICALLY-FUNCTIONALIZED NANOPARTICLES ORGANIZED ON ONE-DIMENSIONAL CHAINS

(75) Inventors: Jennifer S. Shumaker-Parry, Salt Lake City, UT (US); Rajesh Sardar, Carrboro, NC (US)

(73) Assignee: University of Utah Research Foundation, Salt Lake City, UT (US)

( * ) Notice: Subject to any disclaimer, the term of this patent is extended or adjusted under 35 U.S.C. 154(b) by 212 days.

(21) Appl. No.: 12/361,253

(22) Filed: Jan. 28, 2009

(65) Prior Publication Data
US 2009/0221764 A1 Sep. 3, 2009

Related U.S. Application Data

(60) Provisional application No. 61/024,102, filed on Jan. 28, 2008.

(51) Int. Cl.
*C08G 69/48* (2006.01)

(52) U.S. Cl. ........ 524/439; 524/401; 524/493; 977/783; 977/932; 525/430; 525/50; 525/540; 525/418; 525/471; 525/472; 525/535; 525/534

(58) Field of Classification Search ................. 524/439, 524/401, 493; 525/420, 50, 540, 418, 471, 525/474, 535, 534; 977/783, 932
See application file for complete search history.

(56) References Cited

U.S. PATENT DOCUMENTS

| | | | |
|---|---|---|---|
| 6,599,631 B2 * | 7/2003 | Kambe et al. | 428/447 |
| 7,108,915 B2 * | 9/2006 | Adams et al. | 428/403 |
| 2006/0153929 A1 * | 7/2006 | Drake | 424/600 |
| 2009/0214655 A1 * | 8/2009 | Ganan Calvo et al. | 424/489 |

FOREIGN PATENT DOCUMENTS

| | | |
|---|---|---|
| JP | 2004-098246 | 4/2004 |
| JP | 2005 007549 | 1/2005 |
| JP | 2006-205302 | 8/2006 |
| WO | WO 2008/097328 | 8/2008 |

OTHER PUBLICATIONS

Kendra Snyder, "Nanoparticle Assembly Enters the Fast Lane, Method borrows instructions from molecular code of life", Oct. 11, 2006. www.bnl.gov/bnlweb/pubaf/PR_display.asp?prID=06-112. As accessed on Nov. 26, 2007. pp. 1-2.
Grethcen A. Devries, et al., "Divalent Metal Nanoparticles", Science, vol. 315, Jan. 19, 2007. www.sciencemag.org. pp. 358-361.

(Continued)

*Primary Examiner* — Satya B Sastri
(74) *Attorney, Agent, or Firm* — Thorpe North & Western LLP

(57) ABSTRACT

The invention provides methods and compositions having one-dimensional nanoparticle chains. A one-dimensional nanoparticle chain can comprise a linear substantially non-crosslinked polymer having pendant groups and asymmetrically functionalized nanoparticles attached to the polymer through the pendant groups. Additionally, an asymmetrically functionalized nanoparticle can comprise a nanoparticle core having an outer surface, a primary group of first ligands attached to a substantially continuous primary region of the outer surface, and a secondary group of second ligands attached to a substantially continuous secondary region of the outer surface, such that the primary group of first ligands and the secondary group of second ligands comprise a different ligand population.

25 Claims, 7 Drawing Sheets

OTHER PUBLICATIONS

Daniela Zancet et al., "Electrophoretic and Structural Studies of DNA-Directed Nanoparticle Groupings". J. Phys. Chem. B 2002, 106, 11758-11763.

Bing Li et al., "Immobilizing Au Nanoparticles with Polymer Single Crystals, Patterning and Asymmetric Functionalization". J. Am.Chem. Soc. 2007, 129,12-13.

Xiaoyang Xu et al., "Asymmetric Functionalization of Gold Nanoparticles with Oligonucleotides". J. Am. Chem. Soc. 2006, 128, pp. 9286-9287.

Kie-Moon Sung et al., "Synthesis of Monofuctionalized Gold Nanoparticles by Fmoc Solid-Phase Reactions"., J. Am. Chem. Soc. 2004, 126, 5064-5065.

James G. Worden et al., "Controlled functionalization of gold nanoparticles through a solid phase synthesis approach". Chem. Commun., 2004, 518-519.

Belle Dume, "Nanopolymers make their debut-physicsworld.com" Jan. 19, 2007. http://physicsworld.com/cws/article/news/26852. As accessed on Feb. 14, 2008. 2 pages.

Rajesh Sardar et al, "Versatile Solid Phase Synthesis of Gold Nanoparticle Dimers Using an Asymmetric Functionalization Approach." J. Am. Chem. Soc. 2007, 129, 5356-5357. S1-S6.

Fengwei Huo et al., "Asymmetric Functionalization of Nanoparticles Based on Thermally Addressable DNA Interconnects". Advanced Materials 2006, 18, 2304-2306.

U.S. Appl. No. 12/412,147, filed Mar. 26, 2009, Jennifer S. Shumaker-Parry.

Jeong-Hwan Kim et al., "Sequential Solid-Phase Fabrication of Bifunctional Anchors on Gold Nanoparticles for Controllable and Scalable Nanoscale Structure Assembly." Langmuir 2008, 24, 5667-5671.

Bing Li et al., "Poly(ethylene oxide) Single Crystals as Templates for Au Nanoparticle Patterning and Asymmetrical Functionalization". Macromolecules 2008, 41, 149-155.

Rajesh Sardar et al., "Asymmetrically Functionalized Gold Nanoparticles Organized in One-Dimensional Chains", Nano Letters 2008 vol. 8, No. 2 pp. 731-736.

Haeshin Lee et al., "Direct Visualization of Hyaluronic Acid Polymer Chain by Self-Assembled One-Dimensional Array of Gold Nanoparticles". Macromolecules 2006, 39, 23-25.

Francesco Stellacci. "From Nano-Particles to Nano-Polymers" SuNMaG, The Supramolecular Nano-Materials Group. Department of Materials Science and Engineering, Power Point, MIT, May 17, 2007.

* cited by examiner

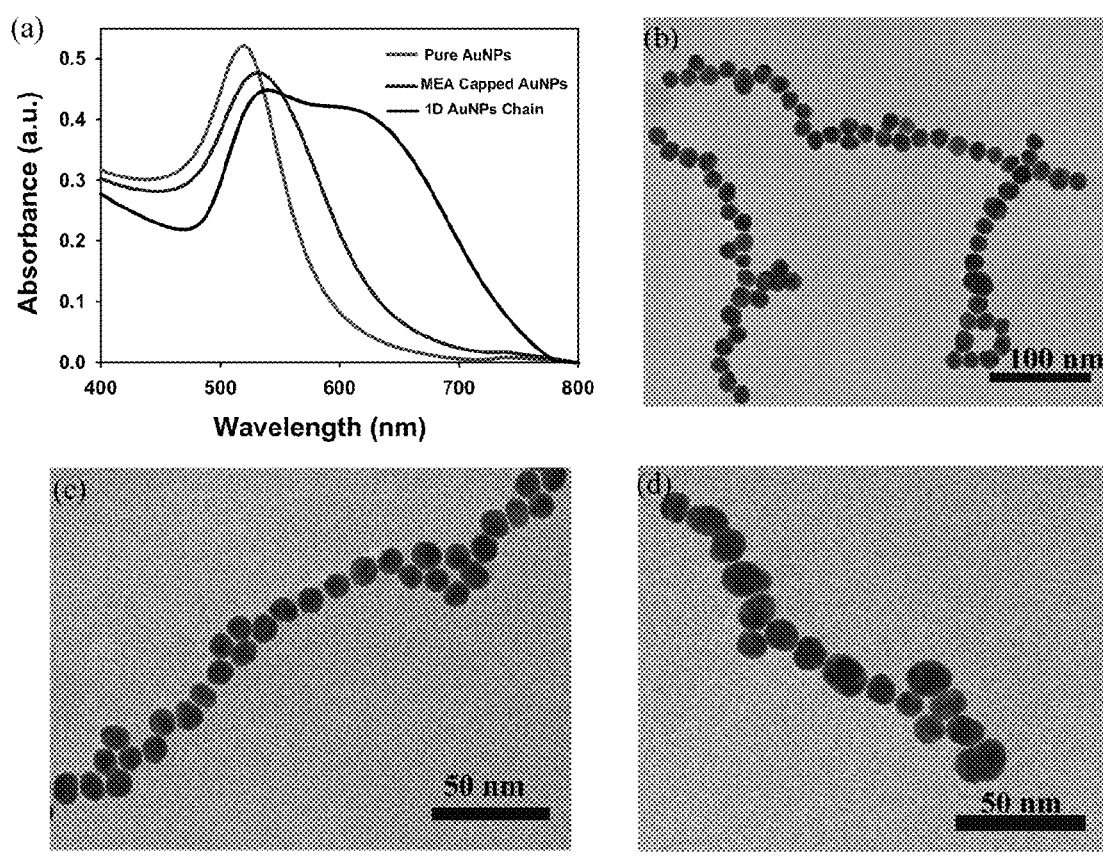
Figures 3A-D

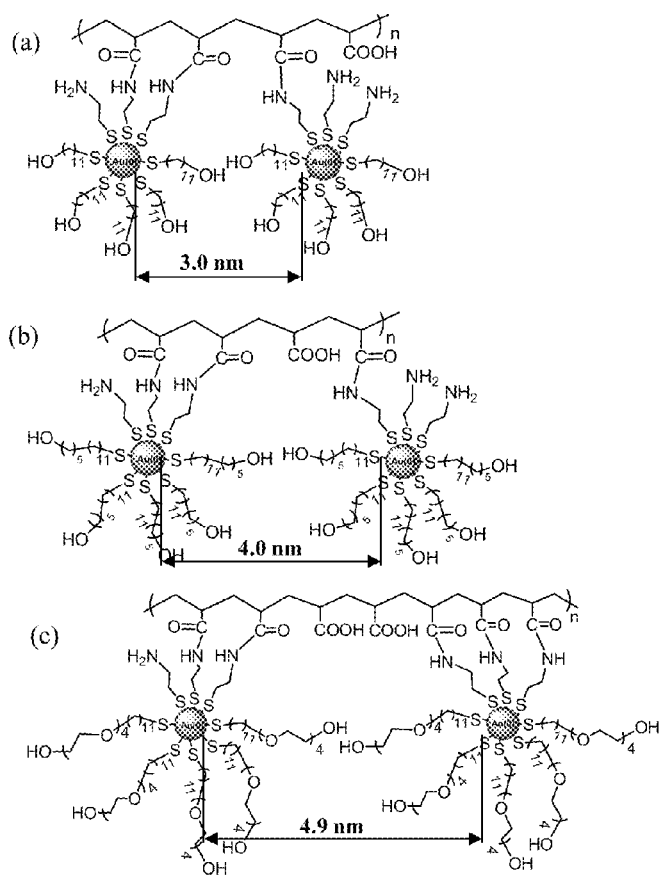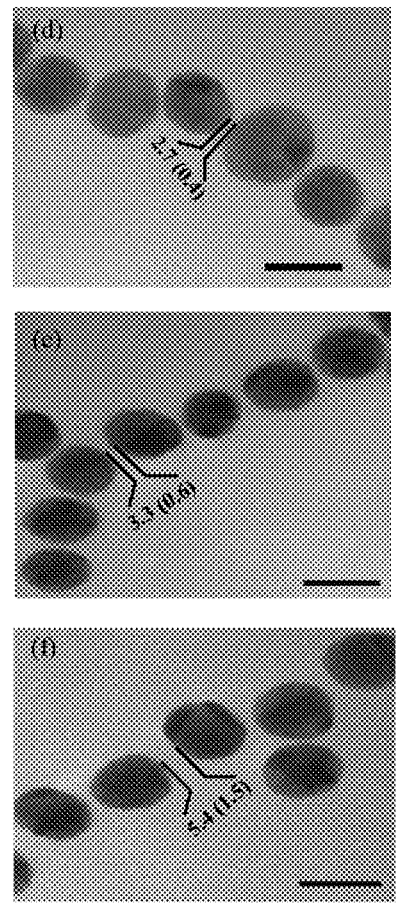
Figures 6A-F

ASYMMETRICALLY-FUNCTIONALIZED NANOPARTICLES ORGANIZED ON ONE-DIMENSIONAL CHAINS

RELATED APPLICATION

This application claims the benefit of copending U.S. Provisional Patent Application Ser. No. 61/024,102 filed on Jan. 28, 2008, which is hereby incorporated by reference in its entirety.

FIELD OF THE INVENTION

The present invention relates generally to asymmetrically functionalized nanoparticles. More particularly, the present invention relates to compositions and methods having asymmetrically functionalized nanoparticles organized in one-dimensional chains. As such, the present invention relates to the fields of chemistry, metallurgy, nanotechnology, and materials science.

BACKGROUND OF THE INVENTION

Nanotechnology refers broadly to a field of applied science and technology whose unifying theme is the control of matter on the atomic and molecular scale, measured in nanometers, and the fabrication of devices within that size range. Examples of nanotechnology in modern use are the manufacture of polymers based on molecular structure, and the design of computer chip layouts based on surface science. Despite the great promise of numerous nanotechnologies such as quantum dots and nanotubes, real commercial applications have mainly used the advantages of colloidal nanoparticles in bulk form, such as suntan lotion, cosmetics, protective coatings, drug delivery, and stain resistant clothing.

Materials reduced to the nanoscale can suddenly show very different properties compared to what they exhibit on a macroscale, enabling unique applications. For instance, opaque substances can become transparent (copper); inert materials can become catalysts (platinum); stable materials can turn combustible (aluminum); solids can turn into liquids at room temperature (gold); insulators can become conductors (silicon). A material such as gold, which is chemically inert at normal scales, can serve as a potent chemical catalyst at nanoscales. Much of the fascination with nanotechnology stems from these unique quantum and surface phenomena that matter exhibits at the nanoscale.

In order to optimize and extend the application of metal nanoparticles, methods must be developed to control the assembly and organization of these materials. Assemblies of nanoparticles also provide optical and electronic properties that are distinct compared to individual particles or disorganized macro-scale agglomeration.

One approach for organizing nanoparticles is to control the composition of the ligand shell around the particles. Typically the ligand shell plays an important role in imparting functionality for specific applications of metal nanoparticles. In most cases, ligands in the shell are selected to chemically define the nanoparticle surface for stabilization in different environments (e.g. aqueous or organic solvents) or to provide attachment sites for probe molecules for sensing applications. Several strategies for controlled assembly of metal nanoparticle are based on tailoring the composition of the ligand shell. Most of these approaches have been based on limiting the number of reactive ligands in the shell in order to control the possible types of assemblies that can be formed. However, such approaches contain various problems including difficult purification, low yield, and size restrictions.

Due to the challenges associated with organized assembly, few methods have been successful in the well-controlled formation of nanoparticle assemblies. Several strategies have employed DNA molecules for nanoparticle assembly based on electrostatic interactions or sequence-specific base pairing. Alternatively, nanoparticle assemblies have been prepared by controlling the composition of the ligand shell using a place exchange process to produce divalent nanoparticles that were assembled by inter-particle covalent linkages. In general, these methods are limited in the size/type of particles that can be assembled and the ligands that can be used. In addition, approaches that involve preparation in organic solvents complicate application of the nanoparticle chains in aqueous-based applications.

As such, research and developmental efforts continue in the field of nanotechnology in the pursuit of new nano-materials, including nanoparticle assemblies, exhibiting unique properties.

SUMMARY OF THE INVENTION

It has been recognized that it would be advantageous to develop asymmetrically functionalized nanoparticles organized in one-dimensional chains.

As such, the present invention provides compositions and methods relating to asymmetrically functionalized nanoparticles organized in one-dimensional chains. In one embodiment, a one-dimensional nanoparticle chain can comprise a linear substantially non-crosslinked polymer having pendant groups and asymmetrically functionalized nanoparticles attached to the polymer through the pendant groups.

In one embodiment, the asymmetrically functionalized nanoparticle can comprise a) a nanoparticle core having an outer surface; b) a primary group of first ligands attached to a substantially continuous primary region of the outer surface; and c) a secondary group of second ligands attached to a substantially continuous secondary region of the outer surface; such that the primary group of first ligands and the secondary group of second ligands comprise a different ligand population.

A method of making one-dimensional nanoparticle chain can comprise a) attaching a nanoparticle core to a substrate such that at least a portion of a primary region on an outer surface of the core is exposed; b) functionalizing at least a portion of the exposed outer surface by reacting the exposed outer surface with a first ligand to form a substantially continuous primary region of the first ligand; c) releasing the nanoparticle core from the substrate to expose a non-functionalized outer surface of the nanoparticle core; d) functionalizing at least a portion of the non-functionalized outer surface by reacting the non-functionalized outer surface with a second ligand to form a substantially continuous secondary region of the second ligand; such that the primary region of the first ligand and the secondary region of the second ligand comprise a different ligand population; and e) attaching the functionalized nanoparticle to a linear substantially non-crosslinked polymer chain having pendant groups by reacting either the first or second ligand of the functionalized nanoparticle with the pendant groups. The first and/or second ligands can be a single ligand or mixture of ligands.

In another embodiment a method of tuning optical properties of a one-dimensional nanoparticle chain can comprise a) choosing a linear substantially non-crosslinked polymer having pendant groups, where the pendant groups having a predetermined spacing along the polymer, to achieve a target optical property; and b) attaching asymmetrically functionalized nanoparticles to the pendant groups, where the asymmetrically functionalized nanoparticles comprise i) a nanoparticle core having an outer surface; ii) a primary group of first ligands attached to a substantially continuous primary region of the outer surface; and iii) a secondary group of second ligands attached to a substantially continuous secondary region of the outer surface; such that the primary group of first ligands and the secondary group of second ligands comprise a different ligand population.

Additional features and advantages of the invention will be apparent from the detailed description which follows, taken in conjunction with the accompanying drawings, which together illustrate, by way of example, features of the invention.

BRIEF DESCRIPTION OF THE DRAWINGS

FIG. 3(A) is a UV-visible absorption spectra of 16-nm-diameter gold nanoparticles at different stages of the chain formation process in accordance with an embodiment of the present invention.

FIG. 3(B) is a TEM image of one-dimensional nanoparticle chains formed by 16-nm-diameter nanoparticles, in accordance with an embodiment of the present invention.

FIG. 3(C) is a TEM image of one-dimensional nanoparticle chains formed by 10-nm-diameter nanoparticles, in accordance with an embodiment of the present invention.

FIG. 3(D) is a TEM image of one-dimensional nanoparticle chains formed by 30-nm-diameter nanoparticles, in accordance with an embodiment of the present invention.

FIG. 6(A) is a schematic representation of the formation of a chain having nanoparticles functionalized with 11-mercapto-1-undecanol (MUOH) ligands with an inter-particle spacing of 3.0 nm, in accordance with an embodiment of the present invention.

FIG. 6(B) is a schematic representation of the formation of a chain having nanoparticles functionalized with 16-hydroxy-1-hexadecanethiol (HHDT) ligands with an inter-particle spacing of 4.0 nm.

FIG. 6(C) is a schematic representation of the formation of a chain having nanoparticles functionalized with 1-mercapto-11-undecyl tetra(ethylene glycol) (MUTEG) ligands with an inter-particle spacing of 4.9 nm.

FIG. 6(D) is a TEM image of one-dimensional nanoparticle chains nanoparticles functionalized with 11-mercapto-1-undecanol (MUOH) ligands with an inter-particle spacing of 2.7 nm, in accordance with an embodiment of the present invention.

FIG. 6(E) is a TEM image of one-dimensional nanoparticle chains nanoparticles functionalized with 16-hydroxy-1-hexadecanethiol (HHDT) ligands with an inter-particle spacing of 3.3 nm, in accordance with an embodiment of the present invention.

FIG. 6(F) is a TEM image of one-dimensional nanoparticle chains nanoparticles functionalized with 1-mercapto-11-undecyl tetra(ethylene glycol) (MUTEG) ligands with an inter-particle spacing of 5.4 nm, in accordance with an embodiment of the present invention.

DETAILED DESCRIPTION

Figure 1:
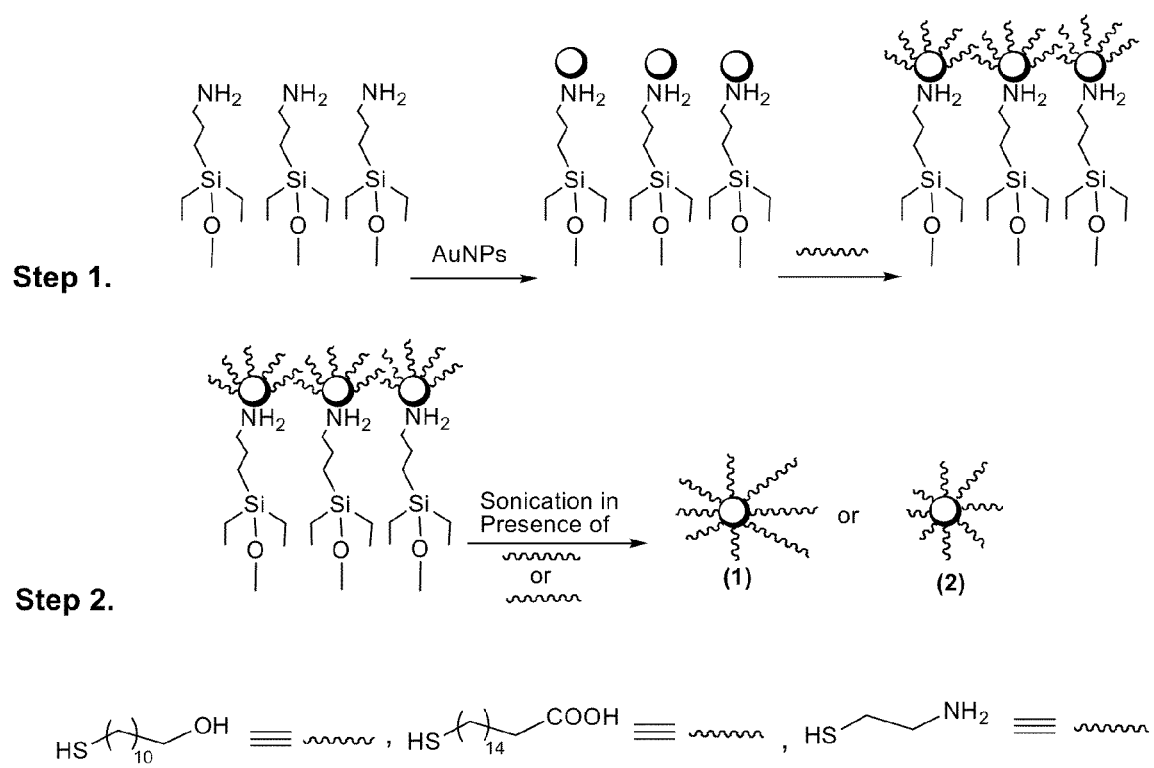
FIG. 1 is a reaction schematic for producing asymmetrically functionalized gold nanoparticles in accordance with an embodiment of the present invention.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

It must be noted that, as used in this specification and the appended claims, the singular forms "a," "an," and "the" include plural referents unless the context clearly dictates otherwise. Thus, for example, reference to "a dimer" includes one or more of such materials, reference to "a ligand" includes reference to one or more of such ligands, and reference to an "attaching" step includes reference to one or more of such steps.

DEFINITIONS

In describing and claiming the present invention, the following terminology will be used in accordance with the definitions set forth below.

As used herein, "nanoparticle" refers to any molecule or compound measuring less than 1 µm. Most often nanoparticles of the present invention are smaller than 100 nm. Such measurements include at least one of or all of: length, width, height, and diameter.

As used herein, "continuous surface" refers to the range of a continuous function from a plane or a connected region in a plane to three-dimensional Euclidean space, where "continuous function" refers to a function which is continuous at each point of its domain.

As used herein, "react" or "reacting" refers to any interaction between the identified materials which results in an association of the identified materials. A reaction of materials can result in formation and/or destruction of chemical bonds, ionic association, or the like.

As used herein, "population" refers to the ligand content or makeup of any given group or region on a surface of a nanoparticle. As such, "population" can refer to the number of ligands, i.e., 25% vs. 75%, and/or the ligand composition; i.e., ligand A vs. ligand B. When describing an asymmetrically functionalized particle, "differing population" or "different population" can refer to the first ligands of the primary group having at least one ligand not in common with the second ligands of the secondary group or can refer to a different concentration of first ligands of the primary group as compared to the second ligands of the secondary group. For example, a primary group having mercaptoethylamine and 11-mercapto-1-undecanol and a secondary group having 16-mercaptohexadecanoic acid and 11-mercapto-1-undecanol can qualify as different populations since the two groups contain at least one ligand not in common (in this example there are two); i.e., mercaptoethylamine and 16-mercaptohexadecanoic acid. Additionally, for example, a primary group containing 75% mercaptoethylamine and 25% 11-mercapto-1-undecanol and a secondary group containing 50% mercaptoethylamine and 50% 11-mercapto-1-undecanol can qualify as different populations since the concentration or ratio of ligands in the respective groups is different.

The present description of "differing populations" or "different populations" can also apply to compositions having more than one asymmetrically functionalized nanoparticle. For instance, the term "differing population" or "different population" can refer to the first and/or second ligands of a first asymmetrically nanoparticle and the first and/or second ligands of a second asymmetrically functionalized nanoparticle that have at least one ligand not in common or can refer to a different concentration or ratio of the first and/or second ligands of the first asymmetrically nanoparticle as compared to the first and/or second ligands of the second asymmetrically functionalized nanoparticle.

Additionally, even though "differing population" or "different population" has been generally defined as different ligands or a differing ratio or concentration of ligands, in one embodiment of the present invention, the compositions and methods described herein may require that the differing population or different population have a different ligand composition regardless of the ligand concentrations or ratios. Additionally, in one embodiment, the compositions and methods described herein may require that the differing population or different population require differing ratios or concentrations of ligands regardless of the ligand composition.

As used herein, "ligand" generally refers to an atom, ion, ligand-receptor (e.g., biomolecules such as proteins), base-pairing as with oligonucleotides that hybridize to form a double-stranded DNA, or molecule that generally donates one or more of its electrons through a coordinate bond to, or shares its electrons through a bond with, one or more central atoms or ions. Additionally, as used herein, a "ligand" is capable of attaching to the surface of a nanoparticle core, as described herein. Such attachment may be by various bonding types; including ionic, covalent, coordinate, or any combination thereof; and may also be by adsorption on the core surface. When referring to a ligand in general throughout the following description, such discussion can be equally applied to the first and/or second ligands as used herein.

As used herein, "multimer" refers to a nano-sized compound having at least two nanoparticles attached thereto. The multimers, described herein, generally have at least two nanoparticles, at least one of which being an asymmetrically functionalized nanoparticle, connected via a spacer group. The multimers can be connected in various configurations. For example, a multimer can be connected linearly, circularly, or in a branched configuration.

As used herein, "cleaving" refers to breaking of the attachment of an immobilized nanoparticle from a substrate. Additionally, "cleaving" may be used to mobilize an otherwise immobilized nanoparticle.

As used herein, "transmission electron microscopy" or "TEM" refers to an imaging technique whereby a beam of electrons is transmitted through a specimen, then an image is formed, magnified, and directed to appear either on a fluorescent screen or layer of photographic film, or to be detected by a sensor.

As used herein, "surface-enhanced Raman spectroscopy" or "SERS" refers to a surface sensitive technique that results in the enhancement of Raman scattering by molecules adsorbed on rough metal surfaces.

As used herein, "surface plasmon resonance" or "SPR" refers to the excitation of surface plasmons by light, such surface plasmons are generally fluctuations in the electron density at the boundary of two materials. As provided herein, such excitation is measured by absorbance.

As used herein, "substantially" or "substantial" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking, the nearness of completion will be so as to have the same overall result as if absolute and total completion were obtained. When referring to "substantially non-crosslinked," the degree of crosslinking is less than 5%. When referring to a region of ligands as being "substantially continuous," such a region would generally not allow for further functionalization in the region, and at the most, would allow less than 2% of additional material in the region. The use of "substantially" is equally applicable when used in a negative connotation to refer to the complete or near complete lack of action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still contain such an item as long as there is no measurable effect thereof.

As used herein, "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited.

As an illustration, a numerical range of "about 10 to about 50" should be interpreted to include not only the explicitly recited values of about 10 to about 50, but also include individual values and sub-ranges within the indicated range.

Thus, included in this numerical range are individual values such as 20, 30, and 40 and sub-ranges such as from 10-30, from 20-40, and from 30-50, etc. This same principle applies to ranges reciting only one numerical value. Furthermore, such an interpretation should apply regardless of the breadth of the range or the characteristics being described.

Invention

The present invention provides methods and compositions having at least one asymmetrically functionalized nanoparticle. Even though the present invention can be discussed in terms of distinct methods and compositions, the following discussions are applicable to each embodiment as provided herein. In other words, when discussing an asymmetrically functionalized nanoparticle in a one-dimensional chain, such a discussion is equally applicable to a method of making such a one-dimensional chain as well as methods of tuning such a one-dimensional chain, and vice versa.

Surprisingly, it has been discovered that nanoparticles can be asymmetrically functionalized using ligands and subsequently organized in one-dimensional chains. As such, the present invention provides compositions and methods relating to asymmetrically functionalized nanoparticles organized in one-dimensional chains. In one embodiment, a one-dimensional nanoparticle chain can comprise a linear substantially non-crosslinked polymer having pendant groups and asymmetrically functionalized nanoparticles attached to the polymer through the pendant groups, e.g. through amide coupling. Alternatively, the polymer may be cross-linked. The one-dimensional nanoparticle chain can have asymmetrically functionalized nanoparticles uniformly spaced at discrete locations on the polymer.

Additionally, although not specifically limited to a particular polymer, as examples, the polymer can comprise or consist essentially of a polymer containing —COOH (carboxylic acid) or —NH$_2$ (amine) groups could be used. This can also be expanded if other linkages were used in conjunction with the asymmetric functionalization process. In other words, as long as the functional group on the nanoparticle can be successfully limited to a small region using the asymmetric functionalization approach, the nanoparticle's functional group can be used to link to the polymer's functional group via many different types of interactions (e.g. electrostatic, ligand-receptor with biomolecules, base-pairing using oligonucleotides) as well as the covalent attachment. As such, the functional group of the nanoparticle can be any group capable of such interactions. Similarly, the pendant groups are not particularly limited and can be any group having a useful functional group which can be utilized in a particular application for bonding, reactivity, etc. The pendant groups can contain an organic functional group that comprises or consists essentially of a member selected from the group consisting of amides, amines, acids, alcohol, esters, ketones, aldehydes, alkanes, alkenes, alkynes, arenes, ethers, heteroatoms, substitutions thereof, derivatives thereof, combinations thereof, and mixtures thereof.

In some embodiments, crosslinking can be present, depending on the particular application and how the crosslinking impacts the properties (e.g., optical properties). In one specific embodiment, the polymer can be substantially free of cross-linking.

In one alternative embodiment, the linear polymer can be a block co-polymer, where one region contains the pendant groups for covalent attachment of asymmetrically functionalized nanoparticles and the other block(s) of the copolymer contains a region inert to nanoparticle assembly. This provides a way to impart two different types of properties to the system or more than two if it is a tri-block copolymer, for example. In another alternative, the linear polymer can include a conductive polymer with the attached nanoparticles. Non-limiting examples of conductive polymers can include polyacetylenes, polypyrroles, polythiophenes, polyanilines, polyfluorenes, poly-3-alkylthiophenes, polytetrathiafulvalenes, polynaphthalenes, poly(p-phenylene sulfide), poly(para-phenylene vinylenes), and copolymers thereof.

In one embodiment, an asymmetrically functionalized nanoparticle can comprise a nanoparticle core having an outer surface, a primary group of first ligands attached to a substantially continuous primary region of the outer surface, and a secondary group of second ligands attached to a substantially continuous secondary region of the outer surface, such that the primary group of first ligands and the secondary group of second ligands comprise a different ligand population.

The nanoparticle core can comprise or consist essentially of a member selected from the group consisting of metals, semi-metals, magnetic materials, and mixtures thereof. In one embodiment, the nanoparticle core can comprise or consist essentially of a member selected from the group consisting of gold, sliver, copper, platinum, semiconductor nanocrystals, bimetallic, metal oxides, nanoshells with a dielectric core and a metal shell, semiconductors such as CdSe, CdSe/CdS, CdTe, ZnSe, PbS, mixtures thereof, and combinations thereof. These nanoparticles can be presented as particles or nanoshells, or having various shapes such as, but not limited to, prisms, cubes, rods, stars, half-shells or half-cups, nanorice, nanoeggs, crescents, etc. For example, a dielectric core with a metal shell around the outside can be suitable. In one embodiment, the nanoparticle core can be gold. Additionally, the nanoparticle core can be any geometric shape or size, e.g. spherical, rod, cube, prism, star, half-shells, cups, oblong, crescents, and the like. In one embodiment, the core can have a single continuous surface across the entire particle. Additionally, the core can be any shape that allows for the nanoparticle to be tunable, as described herein, when attached to a polymer chain, as described herein.

In one embodiment, the core can be spherical. When referring to a spherical embodiment, the core need not be perfectly spherical but may be substantially spherical, i.e., the surface of the core may contain asperities or may be slightly misshapen or irregular. Additionally, the core can be any size such that the resulting particle remains a nanoparticle. As such, the core size may vary from as little as a couple nanometers to as large as several hundred nanometers as measured by diameter or by length. In one embodiment, the core can be from about 2 nm to about 500 nm. In another embodiment, the core can be from about 5 nm to about 100 nm. In yet another embodiment, the core can be from about 5 nm to about 75 nm, about 5 nm to about 50 nm, about 5 nm to about 30 nm, about 10 nm to about 70 nm, about 10 nm to about 50 nm, about 20 nm to about 70 nm, about 20 nm to about 50 nm, or even about 25 nm to about 75 nm.

The ligands described herein, including first and/or second ligands, can comprise or consist essentially of a member selected from the group consisting of: amides, amines, acids, alcohol, esters, ketones, aldehydes, alkanes, alkenes, alkynes, arenes, ethers, substitutions thereof, derivatives thereof, combinations thereof, and mixtures thereof. In one embodiment, the first and/or second ligands can comprise or consist essentially of a member selected from the group consisting of: 11-mercapto-1-undeconal, mercaptoethylamine, 1-mercapto-11-undecyl tetra(ethylene glycol), 16-hydroxy-1-hexadecanethiol, 16-mercaptohexadecanoic acid, and particularly 4-aminophenol, 4-aminothiophenol, and 4-nitrothiophenol, mixtures thereof, combinations thereof, and derivatives thereof. A wide range of amine- and carboxylic-acid-terminated alkyl thiols, etc, can also be suitable. Additionally, the first ligands and/or second ligands can comprise or consist essentially of a member selected from the group consisting of hydrophobic ligands, hydrophilic ligands, anionic ligands, cationic ligands, polar ligands, non-polar ligands, monodentate, bidentate, polydentate, biomolecule-based ligands (e.g. DNA or ligand-receptor with proteins and oligonucleotides for hybridization), combinations thereof, and mixtures thereof. The ligands described herein can also be characterized in functional terms. In one embodiment, the ligands can comprise or consist essentially of a member selected from the group consisting of hydrophobic ligands, hydrophilic ligands, anionic ligands, cationic ligands, polar ligands, non-polar ligands, monodentate, bidentate, polydentate, combinations thereof, and mixtures thereof.

As previously discussed, the asymmetrically functionalized nanoparticles can comprise a primary group of first ligands and a secondary group of second ligands. Each of the primary and secondary groups can encompass a portion of the outer surface of the nanoparticles. The relative proportion of coverage for each group can be tailored within certain bounds for particular applications. Furthermore, each group can often be segregated so as to cover distinct and non-overlapping portions of the nanoparticle surface. In one embodiment, the primary group can cover from about 10% to about 90% of the surface. In another embodiment, the primary group can cover from about 50% to about 80% of the surface. Additionally, the secondary group can cover from about 10% to about 90% of the surface. In one embodiment, the secondary group can cover from about 50% to about 80% of the surface. In another embodiment, the primary and secondary groups can each cover about 50% of the surface.

The first ligands can be chosen based on a number of factors. For example, the ligand can be inert to the specific linkage method used. The length of the spacer group can affect packing of the ligands on the surface and changes the "thickness" of the ligand shell which appears to control the spacing between the nanoparticles along the ID chain. The nanoparticles can be stabilized in a particular solvent environment (i.e. OH-termination is good for aqueous environment). The first ligand shell can be composed of a mixture. For example, this mixture can contain a signal molecule, such as a molecule that is Raman active for Surface Enhanced Raman spectroscopy applications or it could be fluorescent for a fluorescence-based application. The mixture can also contain a dilute component that would allow attachment of another entity such as a protein for a variety of applications (e.g., drug delivery). Similarly, the second ligand is selected for the some of the same reasons. The second ligand generally contains a functional group that will allow it to couple with the polymer. Also, in order to avoid particles coupling with each other, in one embodiment, the coupling can be specific to the polymer functional groups.

In addition to the nanoparticles previously described, the present invention provides one-dimensional chains incorporating such nanoparticles. A one-dimensional nanoparticle chain can comprise a linear substantially non-crosslinked polymer having pendant groups; and asymmetrically functionalized nanoparticles attached to the polymer through these pendant groups. The nanoparticles can be any as described herein including mixtures of such particles. As such, the present one-dimensional chains can also include those having asymmetrically functionalized nanoparticles as well as non-functionalized nanoparticles or symmetrically functionalized particles.

In one embodiment, a one dimensional chain can comprise at least one asymmetrically functionalized nanoparticle and a second nanoparticle. In one embodiment, the second particle can be a second asymmetrically functionalized nanoparticle. Additionally, the nanoparticles described herein may be attached to the pendent groups via a spacer group.

In one embodiment, the differences between the two asymmetrically functionalized nanoparticles can be due to differing populations of ligands, different cores, and/or different core sizes. As such, in one embodiment, a one-dimensional chain can have asymmetrically functionalized nanoparticles that can be different but have the same cores. In another embodiment, the nanoparticle core of a first asymmetrically functionalized nanoparticle can be different than the second nanoparticle core of a second asymmetrically functionalized nanoparticle. As such, the nanoparticle core can be of a different material than the second nanoparticle core. Additionally, the first nanoparticle core of the first asymmetrically functionalized nanoparticle can be a different size than the second nanoparticle core of the second asymmetrically functionalized nanoparticle. In one embodiment, the first nanoparticle core and the second nanoparticle core can have a diameter ratio of from about 0.05 to about 10. In another embodiment, the diameter ratio can be about 0.3 to about 10. In yet another embodiment, the diameter ratio can be about 0.1 to about 5, about 1 to about 10, or even about 2 to about 5.

The spacer group can be any an organic chain having a predetermined length. In one embodiment, the predetermined length can be about 0.5 nm to about 1 nm. In another embodiment, the predetermined length can be about 1 nm to about 2 nm, about 2 nm to about 3 nm, or even about 3 nm to about 20 nm. For example, 12 nm can be a multi-layer system with biomolecules such as an antibody tethered to the alkylthiol-based ligand or for oligonucleotides. The spacer group can be functionalized or unfunctionalized, substituted or unsubstituted, and/or linear or branched. In one embodiment, the spacer group can be predominately a carbon chain. Additionally, the carbon chain can optionally contain heteroatoms.

In addition to the compositions described herein, the present invention provides methods associated with one-dimensional chains. In one embodiment, a method of making one-dimensional nanoparticle chain can comprise a) attaching a nanoparticle core to a substrate such that at least a portion of a primary region on an outer surface of the core is exposed; b) functionalizing at least a portion of the exposed outer surface by reacting the exposed outer surface with a first ligand to form a substantially continuous primary region of the first ligand; c) releasing the nanoparticle core from the substrate to expose a non-functionalized outer surface of the nanoparticle core; d) functionalizing at least a portion of the non-functionalized outer surface by reacting the non-functionalized outer surface with a second ligand to form a substantially continuous secondary region of the second ligand; such that the primary region of the first ligand and the secondary region of the second ligand comprise a different ligand population; and e) attaching the functionalized nanoparticle to a linear substantially non-crosslinked polymer chain having pendant groups by reacting either the first or second ligand of the functionalized nanoparticle with the pendant groups. Such a method can further include reacting the first or second ligand with an organic functional group on the pendant group.

Generally, a method of making an asymmetrically functionalized nanoparticle can comprise a) attaching a nanoparticle core to a substrate such that at least a portion of a primary region on an outer surface of the core is exposed; b) functionalizing at least a portion of the exposed outer surface by reacting the exposed outer surface with a first ligand to form a substantially continuous primary region of the first ligand; c) releasing the nanoparticle core from the substrate to expose a non-functionalized outer surface of the nanoparticle core; and d) functionalizing at least a portion of the non-functionalized outer surface by reacting the non-functionalized outer surface with a second ligand to form a substantially continuous secondary region of the second ligand, such that the primary region of the first ligand and the secondary region of the second ligand comprise a different ligand population. Such a method is further illustrated in FIG. 1. In one embodiment, a suspension of one-dimensional nanoparticle chains can be made by the previously discussed method, and can be substantially free of aggregates.

Generally, the nanoparticle core can be attached through an organic functional group on the substrate; however, this is not required. Any means to immobilize the nanoparticle core may be used in conjunction with the methods of the present invention, e.g. electrostatic interactions, ligand-receptor interactions, and the like. Once immobilized, the exposed outer surface can be functionalized by reacting a functional group of the first ligand with the exposed outer surface. The functional group can be any organic functional group, including, without limitation, amides, amines, acids, alcohol, esters, ketones, aldehydes, alkanes, alkenes, alkynes, arenes, ethers, heteroatoms, substitutions thereof, derivatives thereof, combinations thereof, and mixtures thereof. After functionalizing a portion of the surface of the nanoparticle or a region of the surface of the nanoparticle, the nanoparticle can then be released from the substrate or otherwise mobilized. Generally, such functionalization can be in a substantially continuous region. In other words, the portion of the surface that is exposed to the ligands can generally be reacted with the ligands; however, such a reaction can be stoichiometrically controlled to provide a region that is not continuous. For example, providing small amounts of ligands may result in a primary region having a first ligand non-continuously attached to the surface followed by a second ligand reaction on the remaining non bound surface. Such a reaction scheme could provide a substantially continuous region of mixed ligands.

In one embodiment, the nanoparticle core having a substantially continuous primary region of a first ligand can be released from the substrate by cleaving the nanoparticle from the substrate. Such cleaving may be accomplished by any mechanical, physical, and/or chemical force depending on the nature of the interaction (as mentioned above) environmental changes can be used, such as a pH change, a salt concentration change, or even a chemical cleavage. In one embodiment, cleaving can be achieved by sonicating the nanoparticle core. Once the nanoparticle core is release from the substrate or otherwise mobilized, at least a portion of the non-functionalized outer surface can be functionalized by reacting a functional group of a second ligand with the at least a portion of the non-functionalized outer surface. As discussed above, subsequent functionalization of the non-functionalized outer surface can be a mixture of ligands or a single type of ligand. Additionally, once two regions of the outer surface of the core have been functionalized, the nanoparticle may contain additional non-functionalized surface areas. If such areas are present, they may be further functionalized or may be left unfunctionalized in accordance with the methods and compositions discussed herein. Additionally, as discussed herein, the first and second substantially continuous regions can have different populations.

In addition to synthesizing one-dimensional chains having asymmetrically functionalized nanoparticles, the present invention can include tuning optical or other properties of a one-dimensional nanoparticle chain for specific applications. A method of tuning optical properties of a one-dimensional nanoparticle chain can comprise a) choosing a linear substantially non-crosslinked polymer having pendant groups, said pendant groups having a predetermined spacing along the polymer, to achieve a target optical property; and b) attaching asymmetrically functionalized nanoparticles to the pendant groups, where the asymmetrically functionalized nanoparticles can comprise i) a nanoparticle core having an outer surface; ii) a primary group of first ligands attached to a substantially continuous primary region of the outer surface; and iii) a secondary group of second ligands attached to a substantially continuous secondary region of the outer surface; such that the primary group of first ligands and the secondary group of second ligands comprise a different ligand population. Such a method can further comprise predetermining an amount of spacing between adjacent asymmetrically functionalized nanoparticles. Further, the predetermined spacing can be about 0.5 nm to about 500 nm.

The target optical property can be any optical property associated with one-dimensional chains having asymmetrically functionalized nanoparticles. In one embodiment, the target optical property is absorbance. The property generally relates to tuning the localized plasmon resonance properties. These can include the extinction efficiency, the wavelength position of the plasmon band, and the localized electromagnetic field enhancements. Such properties are generally specific to metal nanoparticles. Other properties can include fluorescence enhancement (also due to the plasmon position and the local electromagnetic field enhancements). The present invention provides a way to organize the particles to provide a known amount of particles per unit of area and allows a single chain to provide a higher signal due to multiple particles being present compared to using a single particle.

Generally, the present invention demonstrates how asymmetrically-functionalized metal nanoparticles can be used as versatile building blocks for controlled organization by producing one-dimensional nanoparticle chains using a polymer as a template for assembly. The organization of nanoparticles in one-dimensional chains provides a way to tune the optical properties of the one-dimensional nanoparticle chains. For example, localized surface plasma resonance (LSPR) coupling between particles can occur in a nanoparticle chain in the near-field region and that electromagnetic energy can propagate over a distance of a few hundred nanometers to create a plasmon-based waveguide. Organizing nanoparticles into one-dimensional chains with controlled interparticle spacing can aid the development of nanoparticle-based components for miniaturized photonics devices. In one embodiment, the interparticle spacing, or predetermined spacing as discussed herein, between two adjacent asymmetrical nanoparticles on a one-dimensional chain can be about 0.5 nm to about 500 nm. In another embodiment, the interparticle spacing, or predetermined spacing, can be about 5 nm, or greater. In another embodiment, the spacing can be about 4 nm, or 3 nm, or less. The formation of well-organized nanoparticle-polymer composite materials also may have application in sensing and drug delivery. For metal nanoparticles, a plasmon resonance wavelength tunability range can include the visible and near infrared, e.g. 400-800 or 600-800 nm.

The present methods of forming one-dimensional nanoparticle chains can also use an aqueous-based synthesis providing for a versatile, environmentally friendly process and can facilitate applications in biotechnology. The assembly process can produce a composite material that could provide dual advantages for structural (i.e., provided by the polymer) and electronic or optical (i.e., provided by the nanoparticles) properties. The method can also be applicable for a wide size range of nanoparticles, including those of 10-30 nm. Furthermore, control of the inter-particle spacing by varying ligands of the functionalized on the nanoparticle can allow for further tuning of desired properties. Specifically, such control over particle spacing can be very useful in studying and tuning optical and electronic properties for many applications including device fabrication. Additionally, one-dimensional nanoparticle chain formation can be broadly applicable for other types of nanoparticles with different sizes, shapes, or composition (e.g., semiconductor or magnetic).

Other fields of interest that are contemplated herein include in vivo imaging, drug delivery and disease therapy (cancer therapy with nanoshells). Also magnetic and semiconductor applications can be useful such as imaging, solar energy conversion, and the like. For example, sensing based on magnetic readouts, light guiding with metal particles for plasmon-based circuit components, etc.

EXAMPLES

The following examples illustrate various embodiments of the invention. Thus, these examples should not be considered as limitations of the present invention, but are merely in place to teach how to implement the present invention based upon current experimental data. As such, a representative number of systems are disclosed herein.

Example 1

Functionalization of Glass Surfaces and Subsequent Adsorption of Gold Nanoparticles Glass coverslips were functionalized with 3-aminopropyltriethoxy-silane according to known procedures. The coverslips were cleaned by placing them in an aqueous 20% RBS detergent solution heated to 90° C. and sonicating for 5 minutes. The coverslips were copiously rinsed with nanopure water and then immersed in a 1:1 (v/v) solution of methanol and concentrated HCl for 30 minutes. The coverslips were rinsed thoroughly with nanopure water and left to dry overnight in an oven at 60° C. The clean coverslips were then placed in a 10% (v/v) solution of (3-aminopropyl)triethoxysilane in anhydrous ethanol for 30 minutes. The coverslips were sonicated and then rinsed with anhydrous ethanol and dried at 120° C. for 3 h. Finally, the silanized glass coverslips were immersed in aqueous gold nanoparticle solution for 24 h at room temperature.

Example 2

Functionalization of Gold Nanoparticles with 11-mercapto-1-undecanol

A self-assembled monolayer (SAM) of 11-mercapto-1-undecanol (MUOH) was formed on the surface of the gold nanoparticles by incubation of the nanoparticle-coated coverslips from example 1 in a 1 mM solution of 11-mercapto-1-undecanol for 2 h at room temperature. After formation of the 11-mercapto-1-undecanol SAMs, the surface was thoroughly rinsed with ethanol to remove unreacted thiols, dried using nitrogen, and stored at 4° C. in a $N_2$ atmosphere.

Example 3

Asymmetric Functionalization of (11-mercapto-1-undecanol)-capped Gold Nanoparticles from Example 2 with Mercaptoethylamine The 11-mercapto-1-undecanol functionalized gold nanoparticles adsorbed on the silanized glass surface from Example 2 were sonicated for 5 minutes in 5 mL water containing 50 μl of 1 mM of mercaptoethylamine (MEA).

Example 4

Functionalization of Gold Nanoparticles with 16-hydroxy-1-hexadecanethiol

A self-assembled monolayer (SAM) of 16-hydroxy-1-hexadecanethiol was formed on the surface of the gold nanoparticles by incubation of the nanoparticle-coated coverslips from example 1 in a 1 mM solution of 16-hydroxy-1-hexadecanethiol for 2 h at room temperature. After formation of the 16-hydroxy-1-hexadecanethiol SAMs, the surface was thoroughly rinsed with ethanol to remove unreacted thiols, dried using nitrogen, and stored at 4° C. in a $N_2$ atmosphere.

Example 5

Asymmetric Functionalization of (16-hydroxy-1-hexadecanethiol)-capped Gold Nanoparticles from Example 4 with Mercaptoethylamine The 16-hydroxy-1-hexadecanethiol functionalized gold nanoparticles adsorbed on the silanized glass surface were lifted off by sonication for 5 minutes into 5 mL of water containing 50 μl of 1 mM mercaptoethylamine (MEA).

Example 6

Functionalization of Gold Nanoparticles with 1-mercapto-11-undecyl tetra(ethylene glycol)

A self-assembled monolayer (SAM) of 1-mercapto-11-undecyl tetra(ethylene glycol) was formed on the surface of the gold nanoparticles by incubation of the nanoparticle-coated coverslips from example 1 in a 1 mM solution of 1-mercapto-11-undecyl tetra(ethylene glycol) for 2 h at room temperature. After formation of the 1-mercapto-11-undecyl tetra(ethylene glycol) SAMs, the surface was thoroughly rinsed with ethanol to remove unreacted thiols, dried using nitrogen, and stored at 4° C. in a $N_2$ atmosphere.

Example 7

Asymmetric Functionalization of (1-mercapto-11-undecyl tetra(ethylene glycol))-capped Gold Nanoparticles from Example 6 with Mercaptoethylamine The 1-mercapto-11-undecyl tetra(ethylene glycol) functionalized gold nanoparticles adsorbed on the silanized glass surface were lifted off by sonication for 5 minutes into 5 mL of water containing 50 µl of 1 mM mercaptoethylamine (MEA).

Example 8

Synthesis of One-Dimensional Nanoparticle Chains Using the Asymmetrically Functionalized (11-mercapto-1-undecanol/mercaptoethylamine) Gold Nanoparticles of Example 3

A 3-ml aqueous solution of poly(acrylic acid) (0.2 mg/ml) was prepared with constant stirring for 24 h at room temperature. The polymer solution was then reacted with 1 ml of 0.1 M 1-ethyl-3-(3-dimethylaminopropyl)carbodiimide hydrochloride and 1 ml of 0.2 M 1-pentafluorophenol for another 24 h with constant stirring. Into this solution, 5 ml of the asymmetrically functionalized (11-mercapto-1-undecanol/mercaptoethylamine) gold nanoparticles from Example 5 were added and the reaction mixture was stirred for 6 h at room temperature.

Example 9

Synthesis of One-Dimensional Nanoparticle Chains Using the Asymmetrically Functionalized (16-hydroxy-1-hexadecanethiol/mercaptoethylamine) Gold Nanoparticles of Example 5

A 3-ml aqueous solution of poly(acrylic acid) (0.2 mg/ml) was prepared with constant stirring for 24 h at room temperature. The polymer solution was then reacted with 1 ml of 0.1 M 1-ethyl-3-(3-dimethylaminopropyl)carbodiimide hydrochloride and 1 ml of 0.2 M 1-pentafluorophenol for another 24 h with constant stirring. Into this solution, 5 ml of the asymmetrically functionalized (16-hydroxy-1-hexadecanethiol mercaptoethylamine) gold nanoparticles from Example 6 were added and the reaction mixture was stirred for 6 h at room temperature.

Example 10

Synthesis of One-Dimensional Nanoparticle Chains Using the Asymmetrically Functionalized (1-mercapto-11-undecyl tetra(ethylene glycol)/mercaptoethylamine) Gold Nanoparticles of Example 7 and poly(acrylic acid)

A 3-ml aqueous solution of poly(acrylic acid) (0.2 mg/ml) was prepared with constant stirring for 24 h at room temperature. The polymer solution was then reacted with 1 ml of 0.1 M 1-ethyl-3-(3-dimethylaminopropyl)carbodiimide hydrochloride and 1 ml of 0.2 M 1-pentafluorophenol for another 24 h with constant stirring. Into this solution, 5 ml of the asymmetrically functionalized (1-mercapto-11-undecyl tetra (ethylene glycol)/mercaptoethylamine) gold nanoparticles from Example 7 were added and the reaction mixture was stirred for 6 h at room temperature.

Example 12

Synthesis of One-Dimensional Nanoparticle Chains Using Asymmetrically Functionalized (11-mercapto-1-undecanol/16-mercaptohexadecanoic acid) Gold Nanoparticles and poly(allylamine)

Gold nanoparticles (16-nm-diameter) were immobilized on a silanized glass surface and reacted with 1 mM 11-mercapto-1-undecanol for 2 h at room temperature to form a self-assembled monolayer (SAM) on the nanoparticle surface. After formation of the 11-mercapto-1-undecanol SAMs, the surface was thoroughly rinsed with ethanol to remove unreacted thiols, and dried using nitrogen. The nanoparticles were then lifted off of the surface into 5 mL of water containing 50 µl of 1 mM 16-mercaptohexadecanoic acid by sonication for 5 minutes. The asymmetrically functionalized (11-mercapto-1-undecanol/16-mercaptohexadecanoic acid) gold nanoparticles were then reacted with 100 µl of 0.1 M 1-ethyl-3-(3-dimethylaminopropyl)carbodiimide hydrochloride and 100 µl of 0.2 M 1-pentafluorophenol for 2 h at room temperature followed by the addition of 3 mL of 4 mM aqueous solution of poly(allylamine). The reaction mixture was stirred gently at room temperature for 4 h under a nitrogen atmosphere.

Example 13

Figure 2:
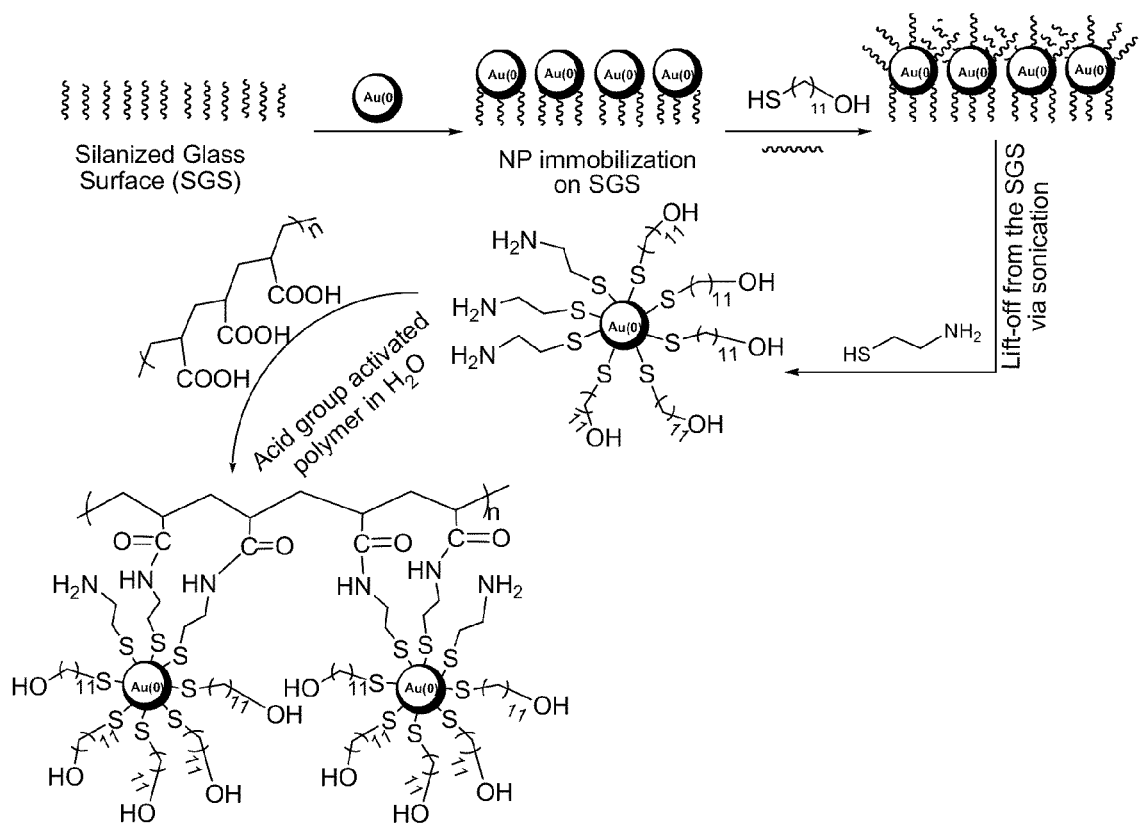
FIG. 2 shows a reaction scheme of the immobilization of citrate-stabilized gold nanoparticles on a silanized glass surface, followed by generation of asymmetrically-functionalized nanoparticles, followed by assembly into a chain structure by covalent attachment to pendent groups along a polymer backbone, in accordance with an embodiment of the present invention.

Synthesis and Analysis of Organized One-Dimensional Chains with Asymmetrical Nanoparticles One-dimensional chains having asymmetrical nanoparticles were assembled in an aqueous solution using a range of nanoparticle sizes. Different size gold nanoparticles can be synthesized using Frens's method as is known in the art. The assembly process can begin with solid phase synthesis of asymmetrically-functionalized nanoparticles in water according to the previously described procedure as shown in FIG. 1. For the present example, citrate-stabilized nanoparticles were immobilized on an amine-terminated silanized glass surface (SGS) where amine groups likely displace citrate groups on the region of the nanoparticle surface that is in contact with the substrate. The nanoparticle-coated SGS was then immersed in an ethanolic solution of 11-mercapto-1-undecanol (MUOH). This step was carried out to displace the remaining citrate shell to create a self-assembled monolayer (SAM) of MUOH molecules on the outer surface of the nanoparticles. In this manner, the substrate and areas facing the substrate are blocked from reaction with additional species. The MUOH-functionalized nanoparticles were then removed from the SGS by sonication in an aqueous solution of 2-mercaptoethylamine (MEA). The MEA molecules bind to the region of the nanoparticle surface which had been associated with the amine-terminated SGS and not accessible to the MUOH molecules during the first functionalization step. The area of the nanoparticle surface associated with the amine groups on the SGS is small compared to the total surface area of the particle. Without intending to be bound by any theory, the MEA molecules are thought to bind to this localized bare region as the particle is released from the substrate, generating asymmetrically-functionalized nanoparticles. The remainder of the nanoparticle surface can be covered by MUOH ligands. In order to assemble the asymmetrically-functionalized nanoparticles, an amide coupling reaction between the amine functional groups localized on the nanoparticles' surfaces and pendent acid groups in poly (acrylic acid) (PAAc) was used, as shown in FIG. 2. An aqueous solution of PAAc was prepared and then reacted with EDAC and PFP to activate the acid groups. Finally, the asymmetrically-functionalized nanoparticles were added to an aqueous solution containing the polymer to form the one-dimensional nanoparticle chains.

The LSPR properties of the gold nanoparticles at different stages of the assembly process were monitored using UV-visible absorption spectroscopy, as shown in FIG. 3A. Before the coupling reaction, the nanoparticles were partially functionalized with MEA and produced a strong LSPR peak at 531 nm. After the reaction of MEA-functionalized particles with PAAc, two distinct absorption peaks are observed, one at 534 nm and the other at 614 nm. The red-shifted peak is likely due to a combination of a change of refractive index of the medium due to the presence of the polymer and also LSPR coupling between the nanoparticles within the one-dimensional chains.

Transmission electron microscopy (TEM) was used to analyze the asymmetrically-functionalized nanoparticles and the one-dimensional nanoparticle chains. TEM analysis shows that the asymmetrically-functionalized nanoparticles prior to assembly with the polymer are dispersed and particle aggregation was not observed. After assembly with the polymer, one-dimensional nanoparticle chains were formed with 14-18 nanoparticles per polymer chain, as shown in FIG. 3B. In some cases, one-dimensional nanoparticle chain networks were observed. While not intending to be bound by any particular theory, these networks could be due to the attachment of two or more acid groups from different polymer chains to one nanoparticle or the entanglement of the polymer chains in solution or during TEM sample preparation. However, no 3-D aggregates were observed. Under similar reaction conditions and identical molar ratio of reagents, one-dimensional nanoparticle chains were synthesized with diameters of 10 nm, as shown in FIG. 3C and 30 nm, as shown in FIG. 3D. The formation of one-dimensional nanoparticle chains occurs when partially amine (MEA) functionalized nanoparticles were combined with EDAC and PFP activated PAAc to form covalent amide linkages between the amine groups on the nanoparticle surface and the carboxylic acid groups of PAAC as shown in the reaction scheme of FIG. 2. The asymmetry of the ligand shell (i.e., the localization of the MEA ligands) leads to a well-controlled one-dimensional chain assembly process with minimal network formation and no 3-D aggregates.

Figure 4A:
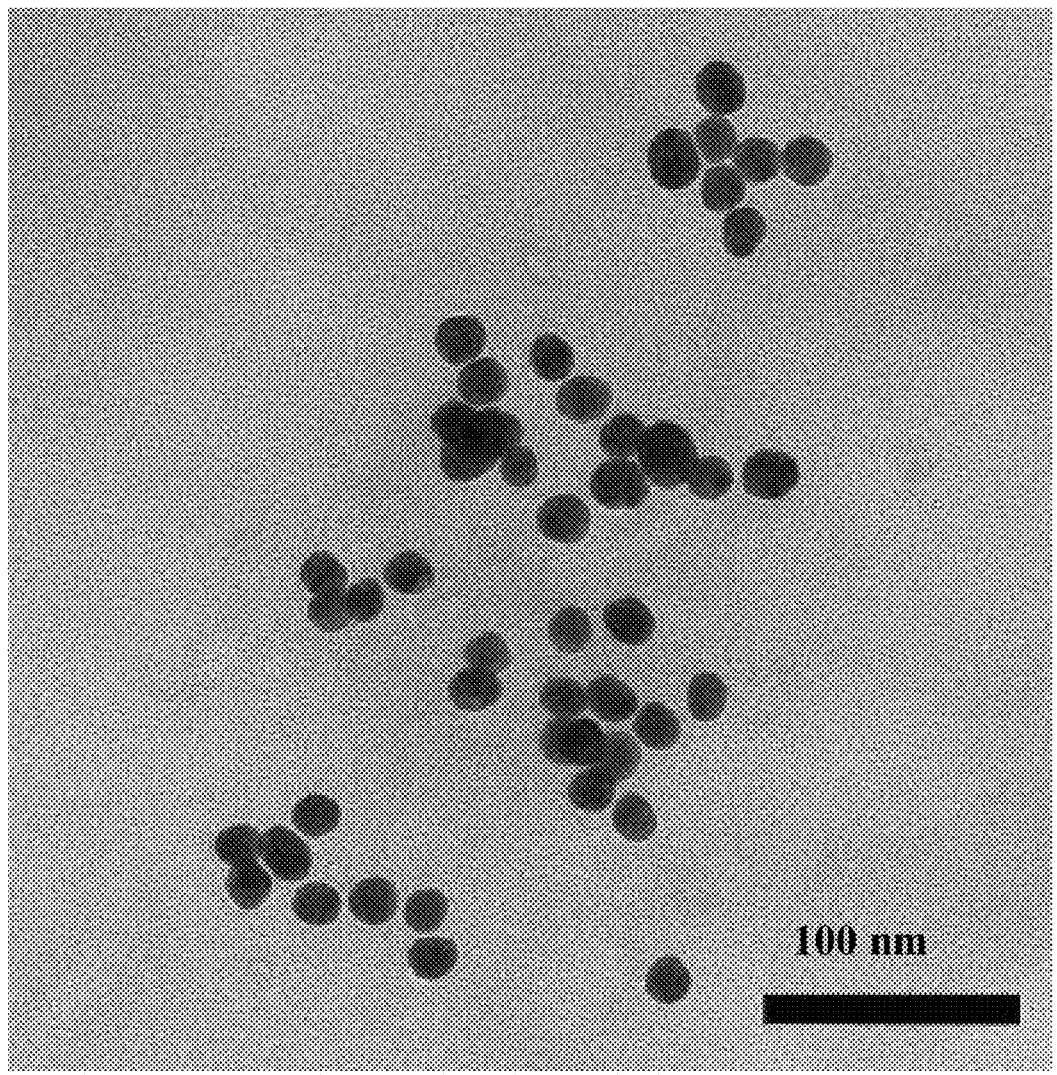
FIG. 4(A) is a TEM image of nanoparticles after ligand exchange with mercaptohexadecanoic acid (MHA), in accordance with an embodiment of the present invention.

Several control experiments provide evidence that the methods of the present invention provide a one-dimensional chain formation process. In the first experiment, free thiols in solution were exchanged with ligands attached to the assembled nanoparticles. During the reaction, the one-dimensional nanoparticle chains were incubated with 16-mercaptohexadecanoic acid (MHA). In the experimental procedure, 2 mL of 1 mM MHA solution was added to 5 mL of a solution of 16-nm-diameter nanoparticle chains and the reaction mixture was stirred at room temperature for 48 h. During the place-exchange reaction, a mixed ligand shell on the gold nanoparticle surface composed of initial capping ligand and the second ligand used in the exchange reaction should have been formed. TEM analysis showed the presence of individual and broken AuNP chains, as shown in FIG. 4A, likely due to ligand exchange between the MHA in solution and the ligands on the nanoparticles' surfaces. The high concentration of MHA molecules present in the solution could easily lead to replacement of the MEA molecules from the surface of the nanoparticles, displacing nanoparticles from the polymer.

Figure 4B:
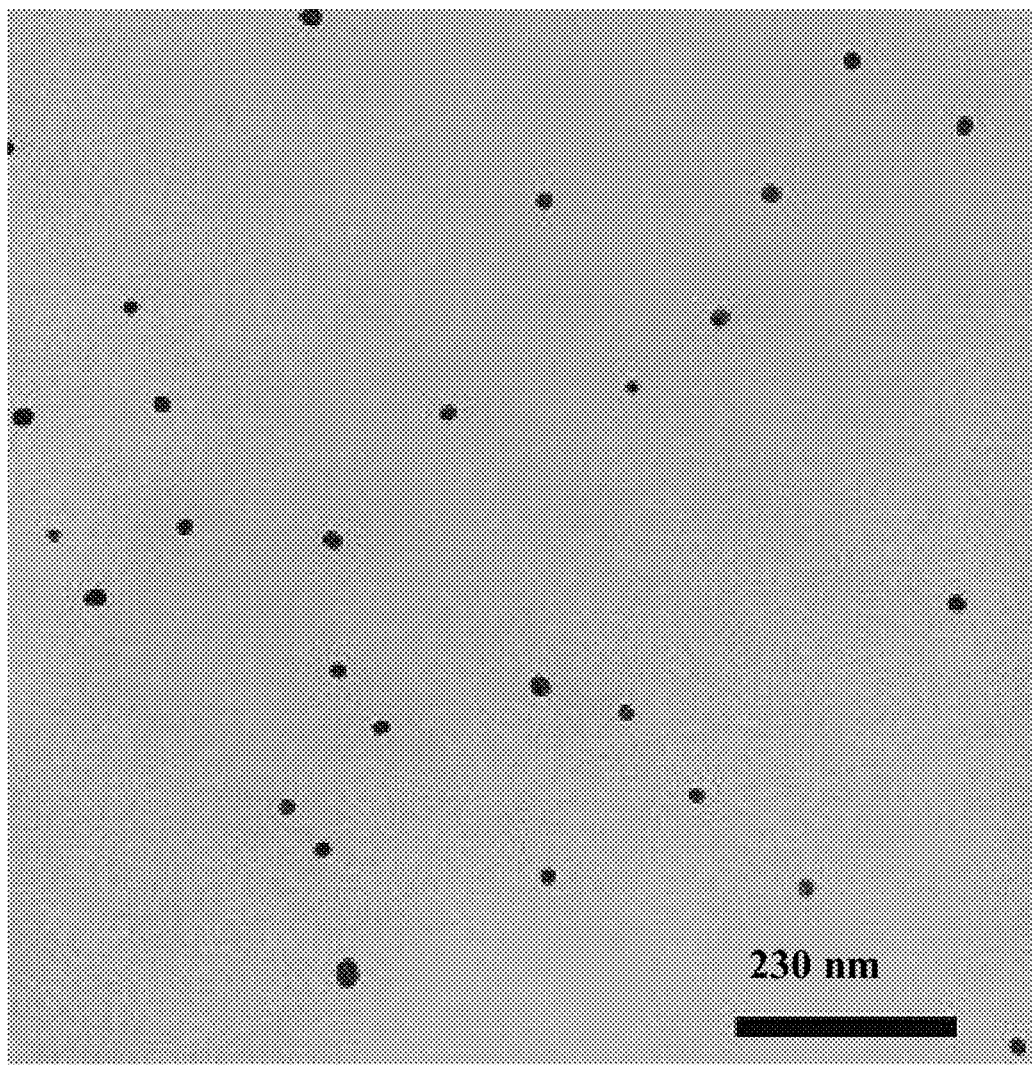
FIG. 4(B) is a TEM image of nanoparticles after mixing citrate-stabilized gold particles with PAAc, in accordance with an embodiment of the present invention.

While not intending to be bound by any particular theory, the present one-dimensional nanoparticle chains are formed by the amine-terminated, asymmetrically-functionalized nanoparticles linked to the polymer through amide bonds with activated acid groups from pendent groups along the polymer backbone. The action of the terminal amine groups present on the asymmetrically-functionalized nanoparticle shell is shown through a control experiment involving the addition of 1 mL of as prepared citrate-stabilized nanoparticles (16 nm diameter) to 3 mL of pure PAAc solution (0.2 mg/mL). The TEM analysis showed the presence of dispersed, individual nanoparticles, as shown in FIG. 4B, with no evidence for chain formation as expected. Additionally, combining partially MEA functionalized AuNPs with the PAAc in solution without EDAC and PFP does not lead to chain formation. Without activating the acid groups on the PAAc, the nanoparticles remain dispersed and there is no evidence of chain formation from TEM analysis. This supports the theory that covalent attachment of the asymmetrically-functionalized nanoparticles to the polymer forms the one-dimensional chains.

Figure 5A:
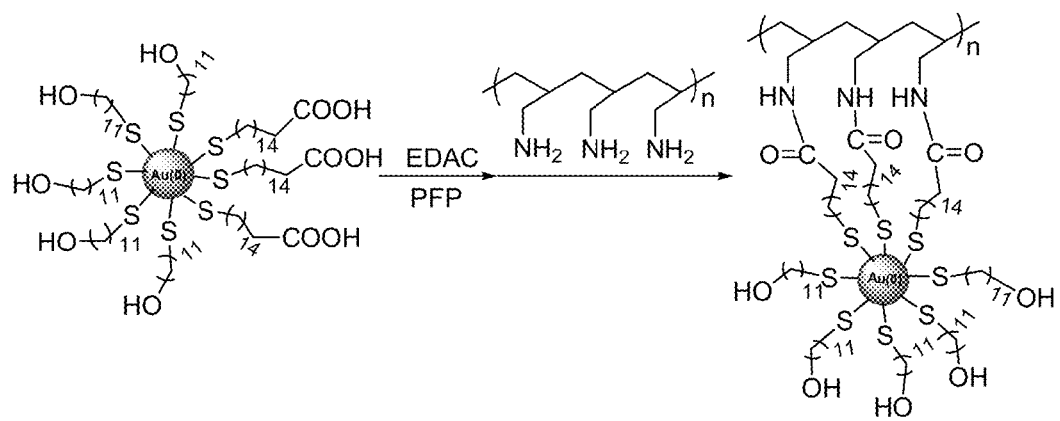
FIG. 5(A) is a schematic diagram of covalent coupling of partially mercaptohexadecanoic acid (MHA) functionalized nanoparticles to amine groups along the backbone of poly(allylamine) in accordance with an embodiment of the present invention.
Figure 5B:
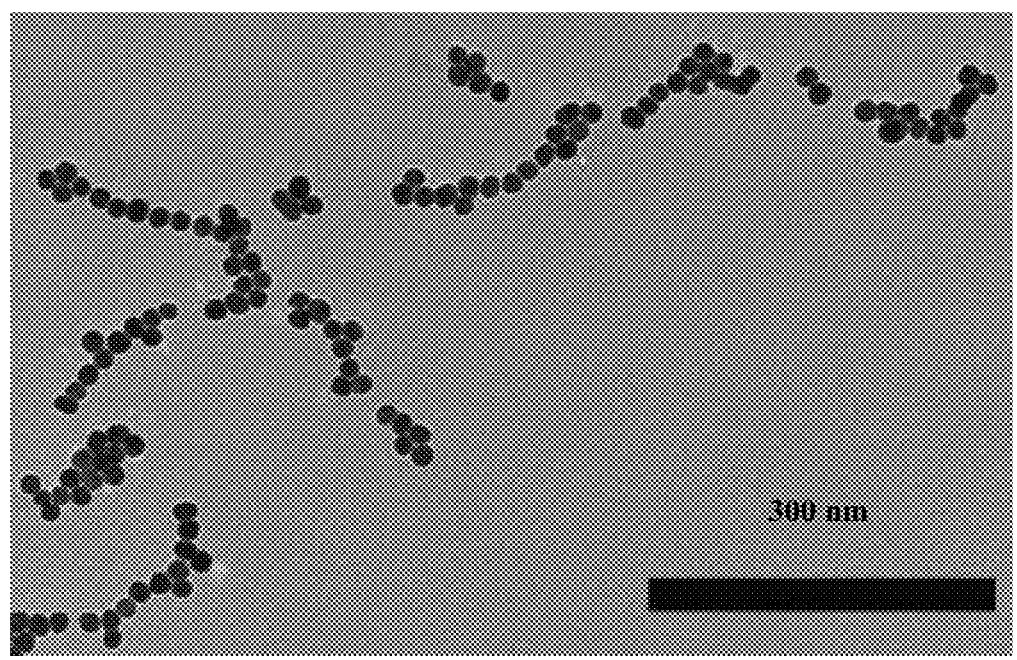
FIG. 5(B) is a TEM image of one-dimensional nanoparticle chains formed by 16-nm-diameter asymmetrically-functionalized nanoparticles, in accordance with an embodiment of the present invention.

To demonstrate the versatility of the one-dimensional nanoparticle chain assembly process and to provide further evidence for specific chemical attachment of the nanoparticles to the polymer, the location of the acid group and the amine group were reversed by including an acid-terminated ligand on the nanoparticle and attaching the particles to the pendent amine groups along the backbone of poly(allylamine) (PAAm). For this experiment, 16-nm-diameter nanoparticles were asymmetrically functionalized with 16-mercaptohexadecanoic acid (MHA) in water shown in FIG. 5A. The resulting nanoparticle solution was then reacted with EDAC in the presence of PFP to activate the acid groups on the nanoparticles' surfaces. An aqueous solution of PAAm was added to the nanoparticle solution. TEM analysis shows the formation of one-dimensional nanoparticle chains with an average of 7 to 11 particles per chain, as shown in FIG. 5B. No 3-D aggregates were observed. The results further support that the activated acid groups on the partially-acid functionalized nanoparticles formed amide bonds with the amine groups on the PAAm.

In one embodiment, control of inter-particle spacing in the one-dimensional nanoparticle chains provides a means to tune the LSPR properties, including the localization of electromagnetic fields. For applications such as surface-enhanced Raman scattering (SERS), the inter-particle spacing between two adjacent particles can be very important. When the particles are in close proximity, the local electromagnetic fields become focused producing a "hot spot" that provides a substantial portion of the enhancement in SERS. As shown in FIG. 6D, the one-dimensional nanoparticle chains exhibit regular inter-particle spacing of 2.7±0.4 nm (i.e., calculated from 100 different particles), which is close to twice the length of an extended MUOH ligand (3.02 nm). This spacing indicates that the nanoparticles form a close-packed assembly with the spacing between neighboring particles determined by the thickness of their MUOH ligand shells. The control of the inter-particle spacing by changing the length of the ligands in the shells is shown in FIGS. 6A-C. When the longer ω-functionalized alkylthiol ligand 16-hydroxy-1-hexadecanethiol (HHDT) is used, the inter-particle spacing increases to 3.3±0.6 nm, as shown in FIG. 6E. This spacing was greater compared to the inter-particle spacing in the one-dimensional chains synthesized in the presence of MUOH, 2.7±0.4 nm, see FIG. 6D. The spacing between the two nanoparticles was further increased by using 1-mercaptoundecyl tetra(ethylene glycol) (MUTEG) as shown in FIG. 6F. A comparative study was made for inter-particle spacings within the one-dimensional chains and the results show that the separation between nanoparticles increases as the length of the ligand increases and the distances measured in the TEM images compare very well with the calculated distances for these ligands, see FIGS. 6D-F.

It is to be understood that the above-referenced arrangements are only illustrative of the application for the principles of the present invention. Numerous modifications and alternative arrangements can be devised without departing from the spirit and scope of the present invention. While the present invention has been shown in the drawings and fully described above with particularity and detail in connection with what is presently deemed to be the most practical and preferred embodiment(s) of the invention, it will be apparent to those of ordinary skill in the art that numerous modifications can be made without departing from the principles and concepts of the invention as set forth herein.

What is claimed is:

1. A one-dimensional nanoparticle chain comprising:
   a) a linear polymer having pendant groups; and
   b) asymmetrically functionalized nanoparticles attached to the polymer through the pendant groups.

2. The one-dimensional nanoparticle chain of claim 1, wherein the linear polymer is substantially non-crosslinked and the asymmetrically functionalized nanoparticles are uniformly spaced at discrete locations on the polymer.

3. The one-dimensional nanoparticle chain of claim 1, wherein the polymer comprises a member selected from the group consisting of a polymer containing —COOH (carboxylic acid), polymer containing —NH$_2$ (amine) groups, and combinations thereof.

4. The one-dimensional nanoparticle chain of claim 1, wherein the pendant groups contain an organic functional group that comprises a member selected from the group consisting of amides, amines, acids, alcohol, esters, ketones, aldehydes, alkanes, alkenes, alkynes, arenes, ethers, heteroatoms, substitutions thereof, derivatives thereof, combinations thereof, and mixtures thereof.

5. The one-dimensional nanoparticle chain of claim 1, wherein the asymmetrically functionalized nanoparticle, comprises
   a) a nanoparticle core having an outer surface;
   b) a primary group of first ligands attached to a substantially continuous primary region of the outer surface; and
   c) a secondary group of second ligands attached to a substantially continuous secondary region of the outer surface;
   wherein the primary group of first ligands and the secondary group of second ligands comprise a different ligand population.

6. The one-dimensional nanoparticle chain of claim 5, wherein the nanoparticle core comprises a member selected from the group consisting of metals, semi-metals, and mixtures thereof.

7. The one-dimensional nanoparticle chain of claim 6, wherein the nanoparticle core comprises a member selected from the group consisting of metals such as gold, silver, platinum, copper, bimetallic, semiconductor, magnetic materials, dielectric core with metal shell, mixtures thereof, and combinations thereof.

8. The one-dimensional nanoparticle chain of claim 5, wherein at least one of the first ligands and second ligands comprise a member selected from the group consisting of amides, amines, acids, alcohol, esters, ketones, aldehydes, alkanes, alkenes, alkynes, arenes, ethers, substitutions thereof, derivatives thereof, combinations thereof, and mixtures thereof.

9. The one-dimensional nanoparticle chain of claim 8, wherein at least one of the first ligands and second ligands comprise a member selected from the group consisting of 11-mercapto-1-undeconal, mercaptoethylamine, 1-mercapto-11-undecyl tetra(ethylene glycol), 16-hydroxy-1-hexadecanethiol, 16-mercaptohexadecanoic acid, 4-aminophenol, 4-aminothiophenol, and 4-nitrothiophenol, mixtures thereof, combinations thereof, and derivatives thereof.

10. The one-dimensional nanoparticle chain of claim 5, wherein at least one of the first ligands and second ligands comprise a member selected from the group consisting of hydrophobic ligands, hydrophilic ligands, anionic ligands, cationic ligands, polar ligands, non-polar ligands, monodentate, bidentate, polydentate, combinations thereof, and mixtures thereof.

11. The one-dimensional nanoparticle chain of claim 5, wherein the primary group covers from about 50% to about 80% of the surface.

12. The one-dimensional nanoparticle chain of claim 5, wherein the primary and secondary groups each cover about 50% of the surface.

13. The one-dimensional nanoparticle chain of claim 5, wherein the core has a single continuous surface.

14. The one-dimensional nanoparticle chain of claim 5, wherein the core is spherical.

15. A method of making a one-dimensional nanoparticle chain, comprising
   a) attaching a nanoparticle core to a substrate such that at least a portion of a primary region on an outer surface of the core is exposed;
   b) functionalizing at least a portion of the exposed outer surface by reacting the exposed outer surface with a first ligand to form a substantially continuous primary region of the first ligand;
   c) releasing the nanoparticle core from the substrate to expose a non-functionalized outer surface of the nanoparticle core;
   d) functionalizing at least a portion of the non-functionalized outer surface by reacting the non-functionalized outer surface with a second ligand to form a substantially continuous secondary region of the second ligand; such that the primary region of the first ligand and the secondary region of the second ligand comprise a different ligand population; and
   e) attaching the functionalized nanoparticle to a linear substantially non-crosslinked polymer chain having pendant groups by reacting either the first or second ligand of the functionalized nanoparticle with the pendant groups.

16. The method of claim 15, wherein the exposed outer surface is functionalized by reacting a functional group of the first ligand with the exposed outer surface.

17. The method of claim 15, wherein the at least a portion of the non-functionalized outer surface is functionalized by reacting a functional group of the second ligand with the at least a portion of the non-functionalized outer surface.

18. The method of claim 15, wherein the first or second ligand is reacted with an organic functional group on the pendant group.

19. The method of claim 15, wherein the substantially continuous primary region of the first ligand covers from about 50% to about 80% of the surface.

20. The method of claim 19, wherein each of the substantially continuous primary region of the first ligand and the substantially continuous secondary region of the second ligand covers about 50% of the surface.

21. The method of claim 15, wherein the nanoparticle core has a single continuous surface.

22. A suspension of one-dimensional nanoparticle chains made by the method of claim 15, wherein the suspension is substantially free of aggregates.

23. A method of tuning optical properties of a one-dimensional nanoparticle chain, comprising
 a) choosing a linear substantially non-crosslinked polymer having pendant groups, said pendant groups having a predetermined spacing along the polymer, to achieve a target optical property; and
 b) attaching asymmetrically functionalized nanoparticles to the pendant groups, the asymmetrically functionalized nanoparticles comprising
  i) a nanoparticle core having an outer surface;
  ii) a primary group of first ligands attached to a substantially continuous primary region of the outer surface; and
  iii) a secondary group of second ligands attached to a substantially continuous secondary region of the outer surface;
 wherein the primary group of first ligands and the secondary group of second ligands comprise a different ligand population.

24. The method of claim 23, wherein the target optical property is absorbance.

25. The method of claim 24, further comprising predetermining an amount of spacing between adjacent asymmetrically functionalized nanoparticles, wherein the predetermined spacing is about 0.5 nm to about 500 nm.

* * * * *